United States Patent [19]
Hammock et al.

[11] Patent Number: 6,150,415
[45] Date of Patent: Nov. 21, 2000

[54] EPOXIDE HYDROLASE COMPLEXES AND METHODS THEREWITH

[75] Inventors: Bruce D. Hammock; Christophe H. Morisseau, both of Davis, Calif.; Jiang Zheng, Boston, Mass.; Marvin H. Goodrow, Winters, Calif.; Tonya Severson; James Sanborn, both of Sacramento, Calif.

[73] Assignee: The Regents of the University of California, Oakland, Calif.

[21] Appl. No.: 09/252,148

[22] Filed: Feb. 18, 1999

Related U.S. Application Data

[63] Continuation-in-part of application No. 08/909,523, Aug. 12, 1997, Pat. No. 5,955,496
[60] Provisional application No. 60/023,397, Aug. 13, 1996, abandoned.

[51] Int. Cl.⁷ ..................................................... A61K 31/17
[52] U.S. Cl. .......................... 514/588; 514/595; 514/598; 514/634; 514/635; 514/663; 514/708
[58] Field of Search ..................................... 514/598, 595, 514/588, 634, 635, 663, 708

[56] References Cited

U.S. PATENT DOCUMENTS 5,445,956  8/1995  Hammock et al. .

OTHER PUBLICATIONS

Abdel–Aal and Hammock, "Use of Transition–State Theory in the Development of Bioactive Molecules," Chapter 9 in *Bioregulators for Pest Control*, ACS Symposium Series No. 276 (based on a symposium held Jun. 24–29, 1984), Hedin, ed., American Chemical Society, Washington, D.C., pp. 135–160, 1985.

Blee and Schuber, "Enantioselectivity of the Hydrolysis of Linoleic Acid Monoepoxides Catalized by Soybean Fatty Acid Epoxide Hydrolase," *Biochemical and Biophysical Research Communications*, 187 (1), pp. 171–177, Aug., 31, 1992.

Cheung et al., "Pesticide Immunoassay as a Biotechnology," Chapter 18 in *The Impact of Chemistry on Biotechnology: Multidisciplinary Discussions*, ASC Symposium Series No. 362, Phillips et al., eds., American Chemical Society, Washington, D.C., pp. 217–229, 1988.

Dietze et al., "Inhibition of Epoxide Hydrolase from Human, Monkey, Bovine, Rabbit and Murine Liver by trans–3–Phenylglycidols," *Comp. Biochem. Physiol.*, 104B (2), pp. 309–314, 1993.

Guo et al., "Characterization of a Tobacco Epoxide Hydrolase Gene Induced During the Resistance Response to TMV," *The Plant Journal*, 15 (5), pp. 647–656, 1998.

Hammock et al., "Epoxide Hydrolases," Chapter 18 in *Comprehensive Technology*, vol. 3 (Biotransformation), Guengerich, ed., Oxford: Pergamon, pp. 283–305, 1997.

Kozak et al., "Inhibitors of Alternative Pathways of Arachidonate Metabolism Differentially Affect Fever in Mice," *Am. J. Physiol.*, 275, pp. 1031–1040, 1998.

Lee et al., "Identification of Non–Heme Diiron Proteins that Catalyze Triple Bond and Epoxy Group Formation," *Science*, 280, pp. 915–918, May 8, 1998.

Mullin, Christopher A., "Adaptive Relationships of Epoxide Hydrolase in Herbivorous Arthropods," *Journal of Chemical Ecology*, 14 (10), pp. 1867–1888, 1988.

Mullin and Hammock, "Chalcone Oxides—Potent Selective Inhibitors of Cytosolic Epoxide Hydrolase," *Archives of Biochemistry and Biophysics*, 216 (2), pp. 423–439, Jul. 1982.

Mumby and Hammock, "Stability of Epoxide–Containing Juvenoids to Dilute Aqueous Acid," *Agricultural and Food Chemistry*, 27 (6), pp. 1223–1228, Nov./Dec. 1979.

Murray et al., "The Expression of Cytochrome P–450, Epoxide Hydrolase, and Glutathione S–Transferase in Hepatocellular Carcinoma," *Cancer*, 71 (1), pp. 36–43, Jan. 1, 1993.

Murray et al., "The Immunohistochemical Localization of Drug–Metabolizing Enzymes in Prostate Cancer," *Journal of Pathology*, 177, pp. 147–152, 1995.

Prestwich and Hammock, "Rapid Purification of Cytosolic Epoxide Hydrolase from Normal and Clofibrate–Treated Animals by Affinity Chromatography," *Proc. Natl. Acad. Sci. USA*, 82, pp. 1663–1667, Mar. 1985.

Theyer et al., "Role of the MDR–1–Encoded Multiple Drug Resistance Phenotype in Prostate Cancer Cell Lines," *The Journal of Urology*, 150, pp. 1544–1547, Nov. 1993.

Wixtrom et al., "Affinity Purification of Cytosolic Epoxide Hydrolase Using Derivatized Epoxy–Activated Sepharose Gels," *Analytical Biochemistry*, 169, pp. 71–80, 1988.

(List continued on next page.)

*Primary Examiner*—James H. Reamer
*Attorney, Agent, or Firm*—Majestic, Parsons, Siebert & Hsue P.C.

[57] ABSTRACT

Biologically stable inhibitors of soluble epoxide hydrolases are provided. The inhibitors can be used, for example, to selectively inhibit epoxide hydrolase in therapeutic applications such as treating inflammation, for use in affinity separations of the epoxide hydrolases, and in agricultural applications. A preferred class of compounds for practicing the invention have the structure shown by Formula 1

FORMULA 1

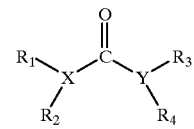

wherein X and Y is each independently nitrogen, oxygen, or sulfur, and X can further be carbon, at least one of $R_1$–$R_4$ is hydrogen, $R_2$ is hydrogen when X is nitrogen but is not present when X is sulfur or oxygen, $R_4$ is hydrogen when Y is nitrogen but is not present when Y is sulfur or oxygen, $R_1$ and $R_3$ are each independently a substituted or unsubstituted alkyl, haloalkyl, cycloalkyl, aryl, acyl, or heterocyclic, or being a metabolite or degradation product thereof.

26 Claims, 2 Drawing Sheets

OTHER PUBLICATIONS

Beetham et al., "cDNA Cloning and Expression of a Soluble Epoxide Hydrolase from Human Liver," *Archives of Biochemistry and Biophysics,* 305 (1), pp. 197–201, Aug. 15, 1993.

Black et al., "Selective Toxicity of N–Sulfenylated Derivatives of Insecticidal Methylcarbamate Esters," *Journal of Agricultural and Food Chemistry,* 21 (5), pp. 747–751, Sep./Oct. 1973.

Bone, Roger C., "Toward an Epidemiology and Natural History of SIRS (Systemic Inflammatory Response Syndrome)," *JAMA,* 268 (24), pp.3452–3455, Dec. 1992.

Borhan et al., "Improved Radiolabeled Substrates for Soluble Epoxide Hydrolase," *Analytical Biochemistry,* 231, pp. 188–200, 1995.

Debernard et al., "Expression and Characterization of the Recombinant Juvenile Hormone Epoxide Hydrolase (JHEH) from *Manduca sexta,*" *Insect Biochemistry and Molecular Biology,* 28, pp. 409–419, 1998.

Demling, Robert H., "The Modern Version of Adult Respiratory Distress Syndrome," *Annu. Rev. Med.,* 46, p. 193–202, 1995.

Dietze et al., "The Interaction of Cytosolic Epoxide Hydrolase with Chiral Epoxides" *Int. J. Biochem.,* 25 (1), pp. 43–52, 1993.

Dietze et al., "Inhibition of Human and Murine Cytosolic Epoxide Hydrolase by Group–Selective Reagents," *Comp. Biochem. Physiol.,* 104B (2), pp. 299–308, 1993.

Dietze et al., "Spectrophotometric Substrates for Cytosolic Epoxide Hydrolase," *Analytical Biochemistry,* 216, pp. 176–187, 1994.

Fahmy et al., "Selective Toxicity of N,N'–Thiodicarbamates," *J. Agric. Food Chem.,* 26 (3), pp. 550–556, 1978.

Fahmy and Fukuto, "N–Sulfinylated Derivatives of Methylcarbamate Esters," *J. Agric. Food Chem.,* 29, pp. 567–572, 1981.

Grant et al., "Molecular Cloning and Expression of Murine liver Soluble Epoxide Hydrolase," *J. Biol. Chem.,* 268 (23), pp. 17628–17633, Aug. 15, 1993.

Harms et al., "Expression of a Flax Allene Oxide Synthase cDNA Leads to Increased Endogenous Jasmonic Acid (JA) Levels in Transgenic potato Plants but Not to a corresponding Activation of JA–Responding Genes," *The Plant Cell,* 7, pp. 1645–1654, Oct. 1995.

Hitz et al., "Expression of a $\Delta 6$–Oleate Desaturase–Related Enzyme from *Vernonia galamenensis* Results in Vernolic Acid Accumulation in Transgenic Soybean," Abstract from the $13^{th}$ International Symposium of Plant Lipids, Sevilla, Spain, Jul. 5–10, 1998.

Jojima et al., "Sugar, Glyceryl, and (Pyridylalkoxy)sulfinyl Derivatives of Methylcarbamate Insecticides," *J. Agric. Food Chem.,* 31, pp. 613–620, 1983.

Kayser et al., "Composition of the Essential Oils of *Pelargonium sidoides* DC. and *Palargonium reniforme* Curt," *Flavour and Fragrance Journal,* 13, pp. 209–212, 1998.

Kiyosue et al., "Characterization of an Arabidopsis cDNA for Soluble Epoxide Hydrolase Gene that is Inducible by Auxin and Water Stress," *The Plant Journal,* 6 (2), pp. 259–269, 1994.

Moghaddam et al., "Novel Metabolic Pathways for linoleic and Arachidonic Acid Metabolism," *Biochimica et Biophysica Acta,* 1290, pp. 327–339, 1996.

Moghaddam et al., "Bioactivation of Leukotoxins to Their Toxic Diols by Epoxide Hydrolase," *Nature Medicine,* 3 (5), pp. 562–566, May 1997.

Morisseau et al., "Mechanism of Mammalian Soluble Epoxide Hydrolase Inhibition by Chalcone Oxide Derivatives," *Archives of Biochemistry and Biophysics,* 356 (2), pp. 214–228, Aug. 15, 1998.

Pinot et al., "Characterization of Epoxide Hydrolase Activity in *Alternaria alternata* f. sp. *lycopersici*. Possible Involvement in Toxin Production," *Mycopathologia,* 140, pp. 51–58, 1997.

Stapleton et al., "Cloning and Expression of Soluble Epoxide Hydrolase from Potato," *The Plant Journal* 6 (2), pp. 251–258, 1994.

Stark et al., "Comparison of Fatty Acid Epoxide Hydrolase Activity in Seeds from Different Plant Species," *Phytochemistry,* 38 (1), pp. 31–33, 1995.

Taton et al., "Inhibition of Higher Plant 2,3–Oxidosqualene Cyclases by Nitroben–Containing Oxidosqualene Analogues," *Phytochemistry,* 43 (1), pp. 75–81, 1996.

Wixtrom and Hammock, "Membrane–Bound and Soluble––Fraction Epoxide Hydrolases: Methodological Aspects," in *Biochemical Pharmacology and Toxicology, Vol. 1: Methodological Aspects of Drug Metabolizing Enzymes,* (Zakin and Vessey, eds.), New York: John Wiley & Sons, pp. 1–93, 1985.

FIG. 1A

HsEH 0.26 μM

EPOXIDE HYDROLASE COMPLEXES AND METHODS THEREWITH

This application is a continuation-in-part of Ser. No. 08/909,523, filed Aug. 12, 1997, now U.S. Pat. No. 5,955,496 Hammock et al., of common assignment herewith, which was based upon provisional application Serial No. 60/023,397, filed Aug. 13, 1996, now abandoned.

This invention was made with U.S. Government support under Grant ES02710, awarded by the National Institutes of Health. The Government has certain rights in this invention.

FIELD OF THE INVENTION

The present invention generally relates to methods of treating epoxide hydrolases so as to form complexes therewith, and more particularly relates to compounds, such as ureas, which complex with epoxide hydrolases and can be used to purify, isolate, or inhibit the epoxide hydrolases so complexed. Where compounds such as ureas are immobilized to water insoluble supports, they can be used in affinity separations of epoxide hydrolases. When compounds such as ureas are administered therapeutically, they are useful in treating inflammatory diseases such as adult respiratory distress syndrome or synergizing anti-neoplastic agents. When applied agriculturally, they will selectively inhibit epoxide hydrolase in pest and crop species.

BACKGROUND OF THE INVENTION

Epoxide hydrolases (EH, E.C.3.3.2.3) are enzymes which catalyze the hydrolysis of epoxides including arene oxides to their corresponding diols by the addition of water. EHs play an important role in the metabolism of a variety of compounds including hormones, fatty acid derivatives, chemotherapeutic drugs, carcinogens, environmental pollutants, mycotoxins, and other harmful foreign compounds.

Several members of this ubiquitous enzyme sub-family have been described based on substrate specificity and subcellular localization. Mammalian EHs include cholesterol epoxide hydrolase, leukotriene $A_4$, hydrolase, hepoxilin hydrolase, microsomal epoxide hydrolase (mEH), and soluble epoxide hydrolase (sEH). The latter two enzymes have been extensively studied and found to have broad and complementary substrate selectivity. The microsomal and soluble forms are known to detoxify mutagenic, toxic, and carcinogenic xenobiotic epoxides, are involved in physiological homeostasis, and both are members of the $\alpha/\beta$-hydrolase fold family.

U.S. Pat. No. 5,445,956, issued Aug. 29, 1995, inventors Hammock et al., discloses recombinant human and mouse soluble epoxide hydrolase. The mouse enzyme provides a rodent model to evaluate for therapeutic development of human soluble epoxide hydrolase inhibitors.

The search for good sEH inhibitors has been actively pursued for the last about twenty years as reviewed by Hammock et al., Comprehensive Toxicology, (Guengerich, F. P., ed.), Pergamon, Oxford, Vol. 3, Chapter 18, pp. 283–305 (1997). Numerous reagents which selectively modify thiols, imidazoles, and carboxyls irreversibly inhibit sEH. Mullin and Hammock, Arch. Biochem. Biophys., 216, pp. 423–429 (1982) disclosed that chalcone oxides were potent inhibitors of sEH, and Dietze et al., Comp. Biochem. Physiolo., 104B, No.2, pp.309–314 (1993) disclosed that trans-3-phenylglycidols were potent chiral inhibitors of sEH.

Copending U.S. Ser. No. 08/909,523, filed Aug. 12, 1997 now U.S. Pat. No. 5,955,496, Hammock et al., suggests the treatment of pulmonary diseases with epoxide hydrolase inhibitors such as chalcone oxides, and describes assays for epoxide hydrolase inhibitors. Among the epoxide hydrolase inhibitors taught are alternative enzyme substrates, such as the epoxide of methyl oleate and other fatty acids and esters or methyl epoxyoctadecenoate and phenyl glycidiols, as well as chalcone oxides.

EH enzymes have been reported to be present in a wide variety of species including bacteria, yeast, fungi, plants, nematodes, insects, birds, fish, and mammals. Indeed, they appear to be present in most, if not all, organisms, and have multiple roles. Plant epoxide hydrolases are also known. For example, fatty acid epoxide hydrolases from apple fruit skin, soybean seedlings, and rice plants have been described. The cDNAs encoding epoxide hydrolase from potato, cress, and tobacco have been isolated and cloned. Stapleton et al., Plant J., 6, pp. 251–258 (1994); Kiyosue et al., Plant J., 6, pp. 259–269 (1994); Guo et al., Plant J., 15, pp. 647–656 (1998). These plant epoxide hydrolases show a high homology with mammalian soluble epoxide hydrolase, but they are 30% shorter on the N-terminus.

Epoxide hydrolases in insects and other arthropods function in the metabolism of endogenous chemical mediators like juvenile hormone and degradation of plant allelochemicals which defend the plant against insects. These enzymes in plants catalyze the hydration of epoxystearic acid to the corresponding $\alpha,\beta$-diols which are important intermediates in the cutin biosynthesis and which have some anti-fungal activity.

Epoxides and diols are key synthetic intermediates in the production of both bulk and speciality organic chemicals. Thus, biosynthetic mechanisms to convert epoxides to diols under gentle, regio and stereospecific conditions are very important. The ability to test if a biosynthetic pathway involves an epoxide by the use of a selective inhibitor can be important in the search for new biosynthetic enzymes and the use of high affinity binding agents in the rapid affinity purification of epoxide hydrolases has proven very important in the study of the mammalian soluble epoxide hydrolases.

The presently known high affinity binding agents for affinity purification of the mammalian soluble epoxide hydrolases include thiols such as benzylthiol, alkyl or terpenoid thiols reacted with epoxy activated SEPHAROSE separation media (SEPHAROSE is available from Pharmacia). These affinity chromatography columns bind a variety of proteins, many of which have a lipophilic catalytic site. The soluble epoxide hydrolase can be selectively eluted from these columns with chalcone oxides, generally as described by Prestwich, Proc. Natl. Acad. Sci. USA, 82, pp. 1663–1667 (1985) and Wixtrom et al., Analyt. Biochem, 169, pp. 71–80 (1988). However, to date there are no affinity purification systems for other epoxide hydrolases which could be used for the initial isolation and cloning of the enzymes, as well as for the isolation of epoxide hydrolases for industrial purposes. New high affinity binding agents for various epoxide hydrolases, particularly for mammalian soluble epoxide hydrolases, remain a useful goal. Also, eluting agents which are competitive, rather then irreversible inhibitors, could be valuable.

SUMMARY OF THE INVENTION

In one aspect of the present invention, a method of treating an epoxide hydrolase is provided that is useful to purify, isolate, or inhibit the target epoxide hydrolase by complexing with a free form or immobilized compound so that the activity of the complexed epoxide hydrolase is modified with respect to enzymatically active, uncomplexed epoxide hydrolase. Compounds useful for forming complexes with epoxide hydrolases in practicing this invention include epoxide hydrolase transition state mimics. For example, ureas, amides, and carbamates can mimic the enzyme transition state or other transient intermediates along the reaction coordinate when these compounds stably interact with the enzyme catalytic site.

A preferred class of compounds with this complexing ability for practice in accordance with the invention has the structure shown by Formula 1.

wherein X and Y is each independently nitrogen, oxygen, or sulfur, and X can further be carbon, at least one of $R_1$–$R_4$ is hydrogen, $R_2$ is hydrogen when X is nitrogen but is not present when X is sulfur or oxygen, $R_4$ is hydrogen when Y is nitrogen but is not present when Y is sulfur or oxygen, $R_1$ and $R_3$ are each independently a substituted or unsubstituted alkyl, haloalkyl, cycloalkyl, aryl, acyl, or heterocyclic.

Where the modified activity of the complexed epoxide hydrolase is enzyme inhibition, then particularly preferred compound embodiments have an $IC_{50}$ (inhibition potency or, by definition, the concentration of inhibitor which reduces enzyme activity by 50%) of less than about 500 $\mu$M. For example, we have discovered that the five compounds listed in Table 1 have an $IC_{50}$ for mouse soluble epoxide hydrolase of less than about 0.1 $\mu$M and less than about 0.8 $\mu$M for human soluble epoxide hydrolase.

TABLE 1

| Inhibitor Structure | No. | Mouse sEH $IC_{50}$ ($\mu$M) | Human sEH $IC_{50}$ ($\mu$M) |
|---|---|---|---|
| | 2 | 0.09 ± 0.01 | 0.16 ± 0.01 |
| | 4 | 0.06 ± 0.01 | 0.13 ± 0.01 |
| | 15 | 0.09 ± 0.01 | 0.72 ± 0.02 |
| | 18 | 0.07 ± 0.01 | 0.15 ± 0.01 |
| | 187 | 0.05 ± 0.01 | 0.42 ± 0.03 |

FORMULA 1

FORMULA 1

In Table 1, the compound 187 is an amide and illustrates that the pharmacophore can be more general than ureas or carbamates.

The enzymes of interest for this invention typically are able to distinguish enantiomers. Thus, in choosing an inhibitor for use for an application in accordance with the invention it is preferred to screen different optical isomers of the inhibitor with the selected enzyme by routine assays so as to choose a better optical isomer, if appropriate, for the particular application. The pharmacophores described here can be used to deliver a reactive functionality to the catalytic site. These could include alkylating agents such as halogens or epoxides or Michael acceptors which will react with thiols and amines. These reactive functionalities also can be used to deliver fluorescent or affinity labels to the enzyme active site for enzyme detection.

Inhibition of soluble epoxide hydrolase can be therapeutically effective to treat an inflammatory disease, such as adult respiratory distress syndrome. This is because suitable epoxide hydrolase inhibitors retard or prevent an inflammatory response in a patient via an inhibition of formation of one or more polyunsaturated lipid metabolites, such as to inhibit the formation of dihydroxy-oxyeicosadienoates, or DiHOxyEDEs in the arachidonic acid series of oxylipins. Arachidonic acid epoxides (EETs) and in some cases the corresponding diols (DHETs) are widely known to be biologically active as well. They are thought to be involved in the onset and severity of fever (Kozak, 1998), they inhibit prostaglandin E2 production in vascular smooth muscle (Fang, 1998), mediate bradykinin induced vasodilation of heart (Fulton, 1998), induce vasodilation (Oltman, 1998; Imaoka, 1998), and have other physiological effects. The soluble epoxide hydrolase appears to bioactivate an inflammatory-derived mediator, which suggests the need for effective and site-specific inhibitors of epoxide hydrolase, such as are provided as one aspect of the present invention.

lases in practicing this invention include epoxide hydrolase transition state dicyclohexyl mimics, such as ureas and carbamates which can mimic the enzyme transition state when they stably interact with the enzyme catalytic site. We have found that analogs of the Formula 1 compound, which can also function as selective inhibitors of soluble epoxide hydrolase, include compounds with the Formula 2 structure (where X, Y, $R_1$, $R_2$, $R_3$, and $R_4$ may be as described for Formula 1) but wherein Z is oxygen or sulfur and W is carbon, phosphorous, or sulfur. An illustrative several such inhibitor compounds of the Formula 2 structure are shown in Table 2. Compound 12 may be converted to the corresponding carbodiimide (compound 1) and then to the corresponding urea (compound 2).

FORMULA 2

TABLE 2

| Inhibitor Structure | No. | Mouse sEH IC$_{50}$ ($\mu$M) | Human sEH IC$_{50}$ ($\mu$M) |
|---|---|---|---|
| cyclohexyl—N=C=N—cyclohexyl | 1 | 0.25 ± 0.02 | 0.47 ± 0.01 |
| cyclohexyl—NH—C(=O)—S—cyclohexyl | 11 | 3.8 ± 0.1 | 7.5 ± 0.4 |
| cyclohexyl—NH—C(=S)—NH—cyclohexyl | 12 | 99 ± 5 | 20 ± 1 |

The inhibitor of epoxide hydrolase can also be used therapeutically to treat fever, inflammatory disease, and hypertension. Thus, inhibitors of the invention act to reduce the conversion of lipid epoxides to the corresponding diols, as in conversion of EEP's to DHET's.

In another aspect of this invention, formation of an epoxide hydrolase complex is useful to purify or to isolate the targeted epoxide hydrolase. For example, the Formula 1 compound may be derivatized so as to be immobilized to a water insoluble support. When one contacts the support with enzymatically active epoxide hydrolase, such as to elute an aqueous solution having epoxide hydrolase through the support, then the complex formation causes a selective separation of the epoxide hydrolase.

Inhibitors, such as certain analogues and active derivatives of the Formula 1 compound, can also be used to elute epoxide hydrolases from these and other supports. As earlier noted, useful compounds to complex with epoxide hydro- Chemically and biochemically a thiourea can be converted to a carbodiimide and the carbodiimide will hydrolyze to the urea. If the N and N' substituents are cyclohexyl then the compound is dicyclohexylcarbodiimide (compound 1).

We believe that the inhibitors described herein are the first biologically stable inhibitors of any epoxide hydrolase. The inhibitors have applications on epoxide hydrolases in mammals, plants, insects, and likely on any organism with an epoxide hydrolase.

Other aspects, advantages, and applications of this invention will become apparent upon reading the specification and the appended claims.

DETAILED DESCRIPTION OF THE PREFERRED EMBODIMENTS

One aspect of this invention pertains to inhibition of epoxide hydrolase, preferably selective inhibition. This means that an inhibitor has a greater inhibitory effect on one EH enzyme than it does on other EH enzymes, and has greater selectivity for EH than for non-EH enzymes.

Particularly preferred practice of this invention is to selectively inhibit soluble EH. Example 5 demonstrates the assay used to determine selective inhibition of soluble EH for a number of compounds in accordance with this invention, whose inhibitory data are set out by Table 4. Selectivity is illustrated by Table 3, where the inhibitor used was compound 2.

TABLE 3

| Enzymes | % Inhibition by 100 μM of 2 |
| --- | --- |
| cytosolic EH | 99.3 ± 0.8 |
| peroxisome EH | 99.6 ± 0.6 |
| microsomal EH | 0.5 ± 0.8 |
| cytosolic GST | 0.8 ± 1.1 |
| microsomal P-450 | 1.7 ± 2.3 |
| microsomal carboxyl-esterase | 3.5 ± 4.7 |
| pepsin | 0.1 ± 0.1 |

As shown by the Table 3 data, compound 2 at a concentration of 100 μM inhibited totally the cytosolic and peroxisome EH activities while no significant inhibition was observed for the other enzyme activities tested. These results illustrate the selective inhibition of soluble EH, present in the cytosol and peroxisome enzymes, by the compounds of the invention. A conclusion from these data is that compound 2 is a potent inhibitor of the cytosolic and peroxisomal EH but not of the other enzymes tested. The $K_i$ calculated for compound 2 with mouse sEH was 22±3 nM.

SUITABLE INHIBITOR EMBODIMENTS

In one aspect of the present invention a method of treating an epoxide hydrolase is provided that is useful to purify, isolate, or inhibit the target epoxide hydrolase by complexing with a free form or immobilized compound so that the activity of the epoxide hydrolase so complexed is modified with respect to enzymatically active, uncomplexed epoxide hydrolase.

A preferred class of compounds with this complexing ability for practice in accordance with the invention has the structure shown by Formula 1.

FORMULA 1

FORMULA 1 wherein X and Y is each independently nitrogen, oxygen, or sulfur, and X can further be carbon, at least one of $R_1$–$R_4$ is hydrogen, $R_2$ is hydrogen when X is nitrogen but is not present when X is sulfur or oxygen, $R_4$ is hydrogen when Y is nitrogen but is not present when Y is sulfur or oxygen, $R_1$ and $R_3$ is each independently H, $C_{1-20}$ substituted or unsubstituted alkyl, cycloalkyl, aryl, acyl, or heterocyclic.

In addition to the compounds in Formula 1 which interact with the enzyme in a reversible fashion based on the inhibitor mimicking an enzyme-substrate transition state or reaction intermediate, one can have compounds that are irreversible inhibitors of the enzyme. The active structures such as those in the Tables or Formula 1 can direct the inhibitor to the enzyme where a reactive functionality in the enzyme catalytic site can form a covalent bond with the inhibitor. One group of molecules which could interact like this would have a leaving group such as a halogen or tosylate which could be attacked in an $S_N2$ manner with a lysine or histidine. Alternatively, the reactive functionality could be an epoxide or Michael acceptor such as a α/β-unsaturated ester, aldehyde, ketone, ester, or nitrile.

Figure 1A:
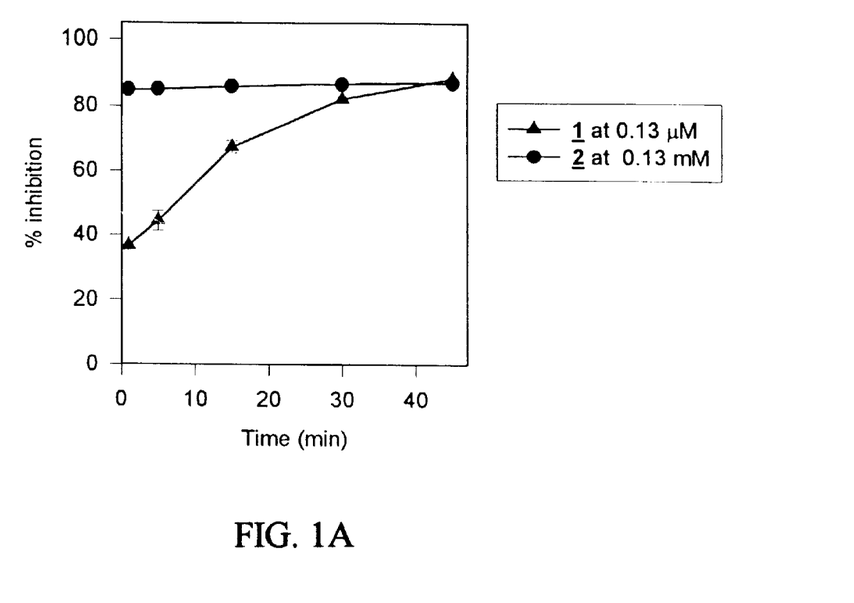
FIGS. 1A and 1B graphically illustrate the effect of time on the inhibition of mouse soluble EH and human soluble EH, respectively, by compounds 1 and 2.
Figure 1B:
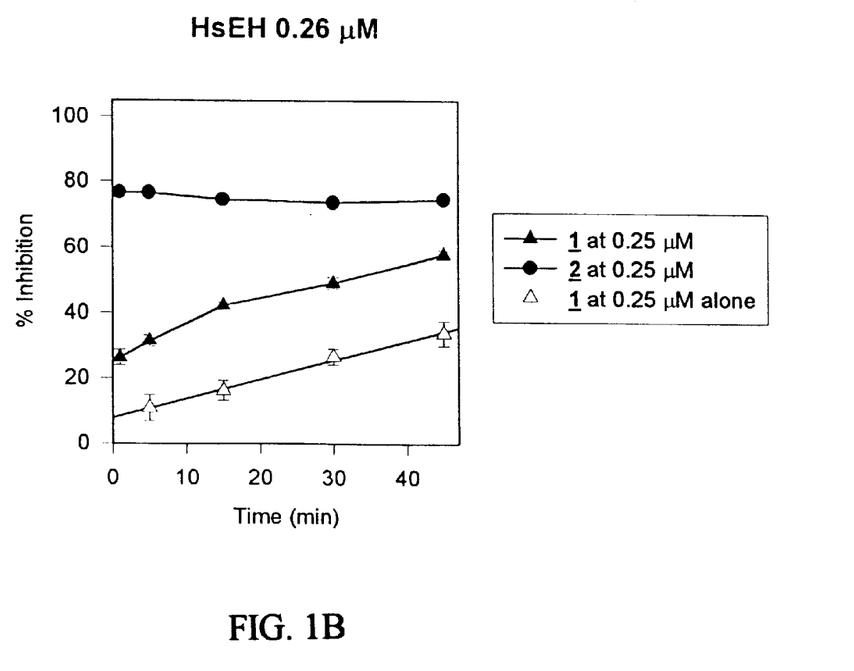
Figure 2:
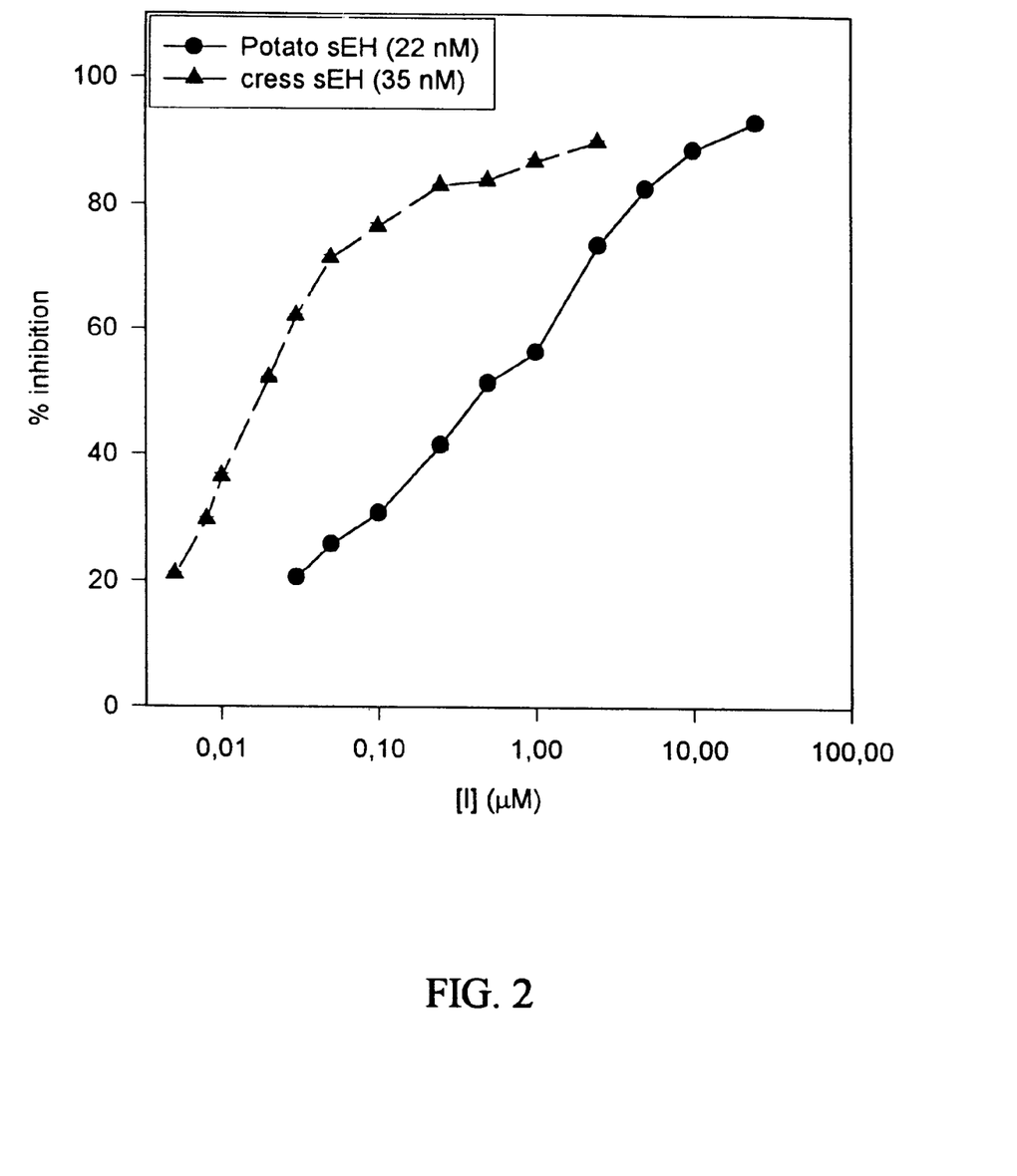
FIG. 2 graphically illustrates the effect of compound 2 on the potato soluble EH (22.5 nM) and cress soluble EH (35 nM).

As shown in FIG. 1, the inhibition of the Mouse sEH by compound 1 increased with the time, while compound 2 inhibition is stable over time. This observation could be explained by the fact that carbodiimide 1 is slowly hydrolyzed to the urea 2 in water solution. These results support the hypothesis that the ureas, carbamates, amides, and related compounds discussed in this invention are acting directly. These results also illustrate the possibility to use carbodiimides as precursor forms of the urea compounds of the invention. Thioureas have in turn been used commercially as precursor forms of carbodiimides.

Further, in addition to the Formula 1 compounds, active derivatives can be designed for practicing the invention. For example, dicyclohexyl thiol urea can be oxidized to dicyclohexylcarbodiimide which, with enzyme or aqueous acid (physiological saline), will form an active dicyclohexylurea. Alternatively, the acidic protons on carbamates or ureas can be replaced with a variety of substituents which, upon oxidation, hydrolysis or attack by a nucleophile such as glutathione, will yield the corresponding parent structure. These materials are known as prodrugs or protoxins (Gilman et al., 1985, *The Pharmacological Basis of Therapeutics*, 7$^{th}$ *Edition*, MacMillan Publishing Company, New York, p. 16.) Esters, for example, are common prodrugs which are released to give the corresponding alcohols and acids enzymatically (Yoshigae et al., *Chirality*, 9, pp. 661–666, 1997). The prodrugs can be chiral for greater specificity. These derivatives have been extensively used in medicinal and agricultural chemistry to alter the pharmacological properties of the compounds such as enhancing water solubility, improving formulation chemistry, altering tissue targeting, altering volume of distribution, and altering penetration. They also have been used to alter toxicology profiles.

There are many prodrugs possible, but replacement of one or both of the two active hydrogens in the ureas described here or the single active hydrogen present in carbamates is particularly attractive. Such derivatives have been extensively described by Fukuto and associates. These derivatives have been extensively described and are commonly used in agricultural and medicinal chemistry to alter the pharmacological properties of the compounds. (Black et al., "Selective Toxicity of N-Sulfenylated Derivatives of Insecticidal Methylcarbomate Esters," *Journal of Agricultural and Food Chemistry*, 21(5), pp. 747–751, 1973; Fahmy et al., "Selective Toxicity of N,N'-thiodicarbamates," *Journal of Agricultural and Food Chemistry*, 26(3), pp. 550–556, 1978; Jojima et al., "Sugar, Glyceryl, and (Pyridylalkoxy)Sulfinyl Derivatives of Methylcarbamates Insecticides," *Journal of Agricultural and Food Chemistry*, 31(3), pp. 613–620, 1983; and Fahmy et al., "N-Sulfinylated Derivative of Methylcarbamate Esters," *Journal of Agricultural and Food Chemistry*, 29(3), pp. 567–572, May–June 1981.)

Such active proinhibitor derivatives are within the scope of the present invention, and the just-cited references are incorporated herein by reference. Without being bound by theory, we believe that suitable inhibitors of the invention mimic the enzyme transition state so that there is a stable interaction with the enzyme catalytic site. The inhibitors appear to form hydrogen bonds with the nucleophilic carboxylic acid and a polarizing tyrosine of the catalytic site.

Where the modified activity of the complexed epoxide hydrolase is enzyme inhibition, then particularly preferred compound embodiments have an $IC_{50}$ (inhibition potency or, by definition, the concentration of inhibitor which reduces enzyme activity by 50%) of less than about 500 $\mu$M.

Metabolites or degradation products of the foregoing Formula 1 compounds or the compounds discussed below with reference to Formula 2 can also be used as inhibitors and form complexes with EH.

Isolation or Purification of Epoxide Hydrolases by Affinity Separation

An aspect of this invention is to provide affinity purification systems for enzymes having an oxyanion hole and a nucleophilic acid in the catalytic site, particularly where the enzyme is an epoxide hydrolase. We believe it likely that the inhibitors shown herein to inhibit soluble EH will also inhibit a broad range of enzymes in the $\alpha/\beta$-hydrolase fold family that have a nucleophilic acid in the catalytic site. Thus, a purification method for an epoxide hydrolase is provided by immobilizing a compound having the Formula 2 structure to a water-insoluble support.

FORMULA 2 wherein Z is oxygen, nitrogen, or sulfur, W is carbon, phosphorous, or sulfur, X and Y is each independently nitrogen, oxygen, or sulfur, and X can further be carbon, $R_1$–$R_4$ is hydrogen, $R_2$ is hydrogen when X is nitrogen but is not present when X is sulfur or oxygen, $R_4$ is hydrogen when Y is nitrogen but is not present when Y is sulfur or oxygen, $R_1$ and $R_3$ is each independently H, $C_{1-20}$ substituted or unsubstituted alkyl, cycloalkyl, aryl, acyl, or heterocyclic.

Suitable water insoluble supports to which the Formula 2 compound are usefully immobilized include epoxy activated SEPHAROSE, amino propyl or hexyl SEPHAROSE, or carboxyl SEPHAROSE. A variety of solid matrices including glass beads, polyvinyl beads, or agarose can be used.

The so-immobilized compounds constitute a suitable packing material for affinity separations, with the immobilized compounds being capable of forming a complex with epoxide hydrolase when an aqueous solution is eluted through a column packed with the separation packing material or in a batch procedure.

Immobilization of the compound will typically be by derivatizing through one of $R_1$ or $R_3$ by well-known methods. For example, Pharmacia Fine Chemicals sells amino propyl or other amino terminal affinity materials (typically under the trademark "SEPHAROSE") and BioRad Laboratories sells agarose gels and beads for various affinity chromatography needs (typically under the trademark "AFFI-GEL"). These materials can be treated with isocyanates, for example, to give stable immobilized urea derivatives in accordance with the invention that will complex with epoxide hydrolases. Alternatively, the Formula 1 compounds can be used to elute epoxide hydrolases from more general affinity columns, such as where a thiol (e.g. benzylthiol) is reacted with epoxy activated "SEPHAROSE" (either gel or beads) prepared by reaction of butane glycol diglycidyl ether. Epoxide hydrolases in an aqueous solution can then be selectively eluted with the Formula 1 derivatized ureas or Formula 2 derivatized compounds in accordance with this invention.

Epoxide Hydrolase Inhibition to Treat Inflammatory Disease

The inflammatory response is one of the most important physiological mechanisms for the maintenance of human health. However, disorders of inflammation or an inappropriate inflammatory response can result in tissue injury, morbidity, or mortality.

Adult respiratory distress syndrome (ARDS) is a pulmonary disease that has a mortality rate of 50% and results from lung lesions that are caused by a variety of conditions found in trauma patients and in severe burn victims. Ingram, R. H. Jr., "Adult Respiratory Distress Syndrome," *Harrison's Principals of Internal Medicine*, 13, p. 1240, 1995. With the possible exception of glucocorticoids, there have not been therapeutic agents known to be effective in preventing or ameliorating the tissue injury, such as microvascular damage, associated with acute inflammation that occurs during the early development of ARDS.

ARDS, which is defined in part by the development of alveolar edema, represents a clinical manifestation of pulmonary disease resulting from both direct and indirect lung injury. While previous studies have detailed a seemingly unrelated variety of causative agents, the initial events underlying the pathophysiology of ARDS is not well understood. ARDS was originally viewed as a single organ failure, but is now considered a component of the multisystem organ failure syndrome (MOFS). Pharmacologic intervention or prevention of the inflammatory response is presently viewed as a more promising method of controlling the disease process than improved ventilatory support techniques. See, for example, Demling, *Annu. Rev. Med.*, 46, pp. 193–203, 1995.

Another disease (or group of diseases) involving acute inflammation is the systematic inflammatory response syndrome, or SIRS, which is the designation recently established by a group of researchers to describe related conditions resulting from, for example, sepsis, pancreatitis, multiple trauma such as injury to the brain, and tissue injury, such as laceration of the musculature, brain surgery, hemorrhagic shock, and immune-mediated organ injuries. Bone, *JAMA*, 268:24, pp.3452–3455, 1992.

We view an important therapeutic application for an aspect of this invention to be in treating diseases of the lung. The lung, with its extensive surface area exposed directly to the environment, is particularly susceptible to oxidant injury and products of inflammation. Since the entire cardiac output passes through the pulmonary artery, the lungs can also be injured by blood-borne agents. The cellular heterogeneity of mammalian lung complicates direct study of these pulmonary cells most susceptible to injury. Furthermore, the complex pulmonary anatomy renders it difficult to distinguish precisely where biological agents are metabolized in lung tissues. The target tissue and sequence of events underlying alveolar edema are not conclusively established; consequently, the interrelationships and relative contributions of endothelial versus epithelial versus inflammatory compartments in mitigating damage to the air-blood barrier remain equivocal.

The ARDS ailments are seen in a variety of patients with severe burns or sepsis. Sepsis in turn is one of the SIRS symptoms. In ARDS there is an acute inflammatory reaction with high numbers of neutrophils that migrate into the interstitium and alveoli. If this progresses there is increased inflammation, edema, cell proliferation, and the end result is impaired ability to extract oxygen. ARDS is thus a common complication in a wide variety of diseases and trauma. The only treatment is supportive. There are an estimated 150,000 cases per year and mortality ranges from 10% to 90%.

The exact cause of ARDS is not known. However it has been hypothesized that over-activation of neutrophils leads to the release of linoleic acid in high levels via phospholipase $A_2$ activity. Linoleic acid in turn is converted to 9,10-epoxy-12-octadecenoate enzymatically by neutrophil cytochrome P-450 epoxygenase and/or a burst of active oxygen. This lipid epoxide, or leukotoxin, is found in high levels in burned skin and in the serum and bronchial lavage of burn patients. Furthermore, when injected into rats, mice, dogs, and other mammals it causes ARDS. The mechanism of action is not known. However, the leukotoxin diol produced by the action of the soluble epoxide hydrolase appears to be a specific inducer of the mitochondrial inner membrane permeability transition (MPT). This induction by leukotoxin diol, the diagnostic release of cytochrome c, nuclear condensation, DNA laddering, and CPP32 activation leading to cell death were all inhibited by cyclosporin A which is diagnostic for MPT induced cell death. Actions at the mitochondrial and cell level were consistent with this mechanism of action suggesting that the inhibitors of this invention could be used therapeutically with compounds which block MPT.

Therapeutic or pharmaceutical compositions of the invention that contains the inhibitors may be prepared by any of the various methods well known. Typically, the inhibitor is formulated so as to suitable for oral or parenteral administration and is typically dissolved or dispersed in a physiologically tolerable carrier or diluent. As one example, an inhibitor can be dissolved or dispersed in a liquid composition such as sterile suspension or solution or as an isotonic preparation. Particularly well suited are injectable medium formulated with buffered or unbuffered isotonic and sterile saline or glucose solution. For in vitro use was in which inhibition of the activity of the target epoxide hydrolase may be monitored by the lessening of the degree of inflammation are well known. The amount of therapeutic inhibitor administered can be by a single administration or a submultiple of the total amount. In addition, multiple administrations over a period of several days, weeks, or months are contemplated.

The active agent can also be used in compositions such as tablets or pills, preferably containing a unit dose, and may be mixed with conventional tableting ingredients. Actual dosage levels of the epoxide hydrolase inhibitor can be varied to obtain the desired therapeutic response for a particular composition and method of administration. The total daily dose administered is contemplated to be from about 0.001 to about 100 mg per kg body weight. However, when practicing the invention a drug like clofibrate, which is known to induce the soluble epoxide hydrolase and cytochrome P-450, and a drug like acetaminophen, which depletes glutathione, should be avoided. This is because we have experimental data suggesting that when glutathione levels are depleted, then leukotoxin becomes more toxic. By contrast, parallel therapies designed to enhance alternate pathways of leukotoxin metabolism such as administration of N-acetylcysteine and glutathione and their ethyl esters should be encouraged.

Example 1 illustrates an in vivo use of the inhibitor embodiment 2 to block animal death induced by leukotoxins/isoleukotoxins or to lengthen lives of mice.

EXAMPLE 1

Male Swiss Webster mice (25–28 g) were purchased from Simonsen, Gilroy, Calif. The animals had free access to water and food. The mice (three in each group) were pretreated i.p. with dicyclohexylurea (compound 2) suspended in corn oil (400 mg/kg, 7 ml/kg) or corn oil as positive controls. After 30 minutes of the pretreatment, the mice were treated intravenously through the tail vein with a 1:1 mixture of leukotoxin/isoleukotoxin methyl esters in ethanol (700 mg/kg, 1.0 ml/kg).

The mice died of respiratory distress after exposure to leukotoxin/isoleukotoxin. The lethal reactions took place sequentially with accelerated breathing, opening of the mouth to assist breathing, and bloody fluid running from the nose. However, pretreatment with N,N'-dicyclohexylurea 2 either blocked the animal death induced by leukotoxin/ isoleukotoxin or lengthened the lives of the mice.

Other Applications for Epoxide Hydrolase Inhibition

Epoxide hydrolase inhibition can be valuable for research purposes, such as to inhibit the microsomal epoxide hydrolase in the Ames' and other toxicity assays where one can increase the sensitivity of the assay for epoxide containing mutagenes and carcinogens and test the hypothesis that the epoxide is involved in toxin action.

Table 4 illustrates a variety of inhibitors together with inhibition data.

TABLE 4

| Structure Inhibitors | nb | Mouse sEH $IC_{50}$ ($\mu$M)* | Human sEH $IC_{50}$ ($\mu$M)* | Rat mEH $IC_{50}$ ($\mu$M)* |
|---|---|---|---|---|
| (dicyclohexylurea structure) | 2 | 0.09 ± 0.01 | 0.16 ± 0.01 | >500 |

TABLE 4-continued

| Structure Inhibitors | nb | Mouse sEH IC$_{50}$ ($\mu$M)* | Human sEH IC$_{50}$ ($\mu$M)* | Rat mEH IC$_{50}$ ($\mu$M)* |
|---|---|---|---|---|
|  | 19 | 5.8 ± 0.4 | 48 ± 3 | 8.3 ± 0.4 |
|  | 57 | 0.06 ± 0.01 | 0.16 ± 0.01 | >500 |
|  | 58 | 0.05 ± 0.01 | 0.09 ± 0.01 | >500 |
|  | 101 | 1.04 ± 0.02 | 5.5 ± 0.1 | 73 ± 1 |
|  | 104 | 0.04 ± 0.01 | 0.29 ± 0.01 | >500 |
|  | 140 | 0.05 ± 0.01 | 0.10 ± 0.01 | >500 |
|  | 161 | 156 ± 3 | 289 ± 7 | >500 |
|  | 167 | 0.39 ± 0.02 | 3.77 ± 0.03 | >500 |
|  | 168 | 0.06 ± 0.01 | 0.12 ± 0.01 | >500 |

TABLE 4-continued

| Structure Inhibitors | nb | Mouse sEH IC$_{50}$ ($\mu$M)* | Human sEH IC$_{50}$ ($\mu$M)* | Rat mEH IC$_{50}$ ($\mu$M)* |
|---|---|---|---|---|
| cyclohexylmethyl-NH-C(=O)-NH-2-naphthyl | 169 | 0.06 ± 0.01 | 0.13 ± 0.01 | >500 |
| n-nonyl-NH-C(=O)-NH-(3-chlorophenyl) | 172 | 0.12 ± 0.01 | 0.30 ± 0.01 | >500 |
| cyclohexylmethyl-NH-C(=O)-NH-(3-chlorophenyl) | 179 | 0.06 ± 0.01 | 0.10 ± 0.01 | >500 |
| cyclohexylmethyl-NH-C(=O)-NH-(4-isopropylphenyl) | 180 | 0.06 ± 0.01 | 0.10 ± 0.01 | >500 |
| cyclohexyl-NH-C(=O)-NH-adamantyl | 192 | 0.05 ± 0.01 | 0.10 ± 0.01 | >500 |
| cyclohexyl-NH-C(=O)-NH-CH$_2$-(4-chlorophenyl) | 193 | 0.05 ± 0.01 | 0.19 ± 0.01 | >500 |
| chlorhexidine-type bis-biguanide | 204 | >250 | 49 ± 7 | 9.9 ± 0.2 |
| cyclohexyl-NH-C(=O)-O-menthyl | 225 | 0.84 ± 0.10 | 1.05 ± 0.03 | >500 |

TABLE 4-continued

| Structure Inhibitors | nb | Mouse sEH IC$_{50}$ ($\mu$M)* | Human sEH IC$_{50}$ ($\mu$M)* | Rat mEH IC$_{50}$ ($\mu$M)* |
|---|---|---|---|---|
| (dicyclohexyl carbamate structure) | 238 | 50 ± 5 | 57 ± 1 | 9.9 ± 0.2 |
| (3,4-dichlorophenyl N-methyl urea structure) | 32 | 108 ± 4 | 47 ± 2 | >500 |
| (N-decyl-N'-ethyl urea structure) | 28 | 5.8 ± 0.4 | 48 ± 3 | 8.3 ± 0.4 |
| (decylamine structure) | 303 | >500 | >500 | 2.67 ± 0.07 |

The Table 4 data illustrates that soluble EH can be inhibited selectively, and compounds 19 and 101 illustrate that microsomal EH can also be inhibited. We believe that these compounds will inhibit a broad range of enzymes in the α/β-hydrolase fold family that have a nucleophilic acid in the catalytic site. The compounds should allow computational chemistry to predict additional active materials.

Further, compound 2 illustrates a very potent inhibitor (preferred embodiment) of the EHs. Compounds 19, 101, 204, and 238 illustrate potent selective inhibitors of the microsomal EH. Compound 225 illustrates that chiral compounds can be used to increase potency and selectivity.

As earlier noted, metabolites or degradation products of the Formula 1 or Formula 2 inhibitors can also form inhibitory complexes with EH and be useful in practicing the invention. Thus, for example, compound 32 of Table 4 is a known metabolite of the herbicide Diuron, and compound 32 inhibits mouse and human soluble epoxide hydrolase. Compound 303 (a degradation product of compound 8) is a better inhibitor of rat microsomal epoxide hydrolase.

Therapeutic uses of epoxide hydrolase inhibition in accordance with the invention may also be useful in conjunction with a cancer therapy. This is because the epoxide hydrolase expression in malignant tumors is one possible mechanism that has been suggested for anti-cancer drug resistance. Murray et al., "The Expression of Cytochrome P-450, Epoxide Hydrolase, and Glutathione S-Transferase in Hepatocellular Carcinoma," *Cancer*, 71, pp. 36–43, 1993; Theyer et al., "Role of the MDR-1-Encoded Multiple Drug Resistance Phenotype in Prostate Cancer Cell Line," *J. of Urology*, 150, pp. 1544–1547, 1993; Murray et al., "The Immunohistochemical Localization of Drug-Metabolizing Enzymes in Prostate Cancer," *J. of Pathology*, 177, pp. 147–152, 1995.

For example, Table 5 illustrates mEH activity for cis-stilbene oxide (Wixtrom and Hammock, 1985, Biochemical Pharmacology and Toxicology, Vol.1: Methodological Aspect of Drug Metabolizing Enzymes (Zakin and Versey, Eds.), John Wiley & Sons, Inc., New York, pp. 1–93) with various cancer cell lines that express microsomal EH. This enzyme is well known to participate in the hepatic metabolism of drug. Thus, the inhibition of this enzyme by Formula 1 or 2 compounds should decrease the metabolism of epoxide containing cancer drugs and thus increase their efficiency.

TABLE 5

| Cell Line | mEH activity (nmol.min$^{-1}$.mg$^{-1}$) |
|---|---|
| Prostate cancer cells | |
| PC-3 | 0.67 |
| DU 145 | 1.80 |
| LNCaP | 1.37 |
| Lung cancer cells | |
| CaLu-1 | 1.53 |
| A-549 | 0.66 |
| Head and neck cancer cells | |
| SQ-20B | 0.37 |
| Ovarian cancer cells | |
| ES-2 | 0.10 |
| SK-OV3 | 1.11 |

As seen by the data of Table 5, microsomal EH activity is significantly expressed in several cancer lines and could participate in the metabolism of cancer drugs such as cyclohexene diepoxide, in malignant tumors. A variety of anti-neoplastic drugs have been developed whose action is based on the alkylating properties of epoxides and diepoxides. Inhibitors of epoxide hydrolase could stabilize these compounds and increase their anti-neoplastic activity.

Uses in Insect Control

Juvenile hormone regulates development of immature insects, the vitellogenin production and uptake into oocytes in reproductive female insects, and dipause in adult insects. Mullin, *J. of Chem. Ecol.*, 14, pp. 1867–1888 (1988) reviewed a variety of epoxide hydrolases then known to metabolize plant allelo chemicals, antifeedents, and essential hormones or precursors for herbivorous arthropods. We contemplate application of the inhibitors herein described together with insecticides that would otherwise be degraded by insectan epoxide hydrolases. The administration of inhibitors so as to cause inhibition of juvenile hormone epoxide hydrolase, for example, in accordance with this invention can disrupt various crucial insect processes. Yet more broadly, action of insecticides degraded by general insectan epoxide hydrolases would benefit if these hydrolases were inhibited so as to enhance the efficacy of the insecticides. One example of such an epoxide containing insecticide is the cyclodiene HEOM. Another agricultural chemical is the epoxide glutathione transferase inhibitor tridiphane. Epoxide hydrolase inhibitors will improve the stability of antifeedents in pest organisms. Table 6 illustrates inhibition data for several inhibitors of this invention. Analogous applications can be made with nematodes and other agricultural, medical, and veterinary pests.

could be produced from such plants, such as vernolic acid. Vernolic acid is an industrial oil useful in manufacturing plastics, paints, and nylon precursors. Inhibiting the soluble epoxide hydrolase of plants can block degradation of epoxides formed biosynthetically, such as to block conversion of the desired vernolic acid in plants to its diol. For example, Blee and Schuber, *Biochemical & Biophys. Res. Comm.*, 187, pp. 171–177 (1992), showed that soybean epoxide hydrolase catalyzes linoleic acid monoepoxides into their corresponding vic-diols.

In carrying out this aspect of the invention, the inhibitors could be sprayed as plant growth regulators on field and row crops, delivered hydroponically, or added to tissue culture fluid in hairy root, cell, or callous culture.

Additionally, inhibiting the soluble epoxide hydrolase of plants can interfere with formation of plant cutin and thus can accelerate penetration of herbicides and other plant growth regulators. When using epoxide hydrolase inhibitors to accelerate or enhance herbicide action or to reduce herbicide resistance, we contemplate application along with an herbicide. Formulations with the epoxide hydrolase inhibitor and herbicides can be prepared for foliage or root

TABLE 6

| Inhibitor Structure | No. | M secta mEH $IC_{50}$ ($\mu$M) |
|---|---|---|
|  | 17 | 28 ± 2 |
|  | 19 | 4.8 ± 0.4 |
|  | 58 | 3.9 ± 0.4 |

The tomato hornworm, *Manduca sexta*, is a pest of tobacco, tomato, and related crops. It also is an insect commonly used as a model in insect biology. As seen by data of Table 6, compounds 17 19, and 58 displayed low $IC_{50}$ for the recombinant microsomal EH thereof, indicating a very good inhibition of this insect EH by the compounds of the invention. This enzyme is involved in the development of this insect by degrading the epoxide of insect juvenile hormone to the inactive diol. Inhibitors of the enzyme will disrupt the development of the insect. Some juvenile hormone mimics or juvenoids such as epofenonane contain the epoxide moiety. Related compounds include R-20458 and Ro 8-4374 in addition to the natural epoxides and diepoxides of the juvenile hormones. (Mumby and Hammock, "Stability of Epoxide Containing Juvenoids to Dilute Aqueous Acid," *J. Agric. Food Chem.*, 27, pp. 1223–1228, 1979.) Selective inhibitors of the microsomal EH acting on juvenile hormone will synergize these pesticidal juvenoids.

Uses with Plants

Recent breakthroughs in work with transgenic plants have suggested that large amounts of unusual plant fatty acids uptake. Further, mycotoxins produced by fungi can be used to increase pathogenesis by destroying cells and to protect the fungal food source. These materials can be highly toxic to humans, domestic animals, and crop plants. For example, *Alternaria alternata f. sp. lycopersici* is a fungal pathogen that causes the Alternaria stem canker disease of tomato. During disease development and in liquid culture, the pathogen secretes host-specific toxins (AAL toxins) which, in purified form, elicit cell death patterns characteristic of the stem canker. The ability of the pathogen to infect leaves, stems, and green fruit of tomato is limited to genotypes that are homozygous for the recessive allele (asc/asc) of the Asc gene. The Asc gene also regulates toxin sensitivity; thus the toxins function as chemical determinants of the stem canker disease. Moreover, AAL toxins, which are members of the same class of sphinganine analog or mycotoxins as fumonisins, inhibit ceramide synthase in rat hepatocytes and induce apoptosis in monkey kidney cells. Unlike the case with fumonisins, the effects of chronic exposure of AAL toxins to animal health are still unresolved. The first of the AAL toxins (TA) was characterized in 1981 and more recently new isomeric toxins were purified and characterized. The presence of one pair of vicinal diols free or esterified, in the structure of all the AAL toxins suggests the possible involvement of an epoxide hydrolase (EH) in their synthesis. This hypothetical mechanism is supported by the fact that one of the oxygen atoms of the diol, came from direct incorporation of atmospheric oxygen and the other came from water.

Accordingly, practice of the invention is also useful to inhibit a fungal epoxide hydrolase, particularly when used in combination with a fungicide. In general, an application rate from about 0.01 to 100 kg/hectare will be suitable for most purposes.

Among the uses contemplated with plants is increasing the yield of vernolic acid, which is used in plastics and the wood industry. Alternatively, the EHs purified by affinity chromatography using the compounds described here, can be used to carry out steps critical to forming important biosynthetic chemicals in both chiral and racemic form. Work is underway in several laboratories to clone into plants both heme and nonheme proteins which will increase the level of epoxylipids in plants. (Lee et al., "Identification of Non-heme Diiron Proteins That Catalyze Triple Bond and Epoxy Group Formation," *Science*, 280, pp. 915–918, 1998; Hitz et al., "Expression of δ-6-oleate Desaturase-related Enzyme from *Vernonia galmenensis* Results in Vernolic Acid Accumulation in Transgenic Soybean," 13th *International Symposium of Plant Lipids*, Sevella, Spain, Jul. 5–10, 1998; and Kinney et al., "Re-engineering Oilseed Crops to Produce Industrial Useful Fatty Acids," Ibid.). Work on the enzyme activity in seed (Stark et al., "Comparison of Fatty Acid Epoxide Hydrolase Activity in Seeds from Different Plant Species," *Phytochemistry*, 38, pp. 31–33, 1995) and the isolation and expression of the corresponding cDNA (Stapleton et al., "Cloning and Expression of Soluble Epoxide Hydrolase from Potato," *Plant J.*, 6(2), pp. 251–258, 1994; and Kiyosue et al., "Characterization of an Aradibopsis cDNA for a Soluble Epoxide Hydrolase Gene that is Inducible by Auxin and Water Stress," *Plant J.*, 6(2), pp. 259–269, 1994) indicates that epoxide hydrolase activity is widespread in plants in general and in their seeds. These levels could be profitably altered by inhibitors, antisense, or over expression of activity to alter relative levels of epoxides and diols. Epoxy lipids and their resulting diols are also thought involved in cross-linking waxes, cutins, and suberins in plant. Thus the compounds influence water retention, susceptibility to disease, and to agricultural chemicals by varying surface layers of plants.

As in mammals oxylipins may be chemical mediators. However, clearly epoxides through an allene oxide synthase increase levels of jasmonic acid (Harms et al., "Expression of a Flax Allene Oxide Synthase cDNA Leads to Increased Endogenous Jasmonic Acid (JA) Levels in Transgenic Potato Plants but Not to a Corresponding Activation of JA-Responding Genes," *The Plant Cell*, 7, pp. 1645–1654, 1995). Inhibiting epoxide hydrolases should result in more endogenous JA in plants with expected changes in plant secondary chemical constituents which will alter susceptibility to pest organisms. The essential oils of plants can be altered by altering the levels of chemical mediators (where epoxide hydrolases can alter levels of essential epoxides) as described above. However, essential oils (terpenes) in plants also can be altered directly by changing the relative levels of enzymes which form epoxides and epoxide hydrolases. Many essential oils are epoxides. These materials are known plant defensive chemicals, but many are also important chemical intermediates and constituents of perfume and cosmetic formulations, such as essential oils of Pelargonium sp. (Kayser et al., "Composition of the essential oils of *Pelargonium sidoides* DC and *Pelargonium reniform* Curt.," *Flavour and Fragrance Journal*, 13, pp. 209–212, 1998). Epoxide hydrolase inhibitors could be used to increase the yield of high value essential oils. As in mammals epoxides are not only involved in terpenes and essential oils in plants, but also in the biosynthesis of squalene, lanosterol, phytosteroids, and cholesterol (Taton et al., "Inhibition of Higher Plant 2,3-oxidosqualene Cyclases by Nitrogen-Containing Oxidosqualene Analogs," *Phytochemishy*, 43, pp. 75–81, 1996).

Preparation of illustrative inhibitors and an assay useful for determining inhibition will now be more specifically described by Examples 2–5, which are to illustrate but not to limit this invention.

EXAMPLE 2
Synthesis of 1-Octyl-3-pentylurea

To 0.262 g (3.00 mmol) of pentylamine in 20 mL of hexane is added 0.53 mL (0.47 g, 3.0 mmol) of octylisocyanate with stirring to eventually produce a white crystalline solid. After standing overnight the mixture is cooled, the solid product collected, and washed with cold hexane. On air drying there is obtained 0.705 g (2.91 mmol, 97%) of 1-octyl-3-pentylurea as very fine white needles, mp 65.0–65.5° C. The material displays a $^{13}$C-NMR and a mass spectrum consistent with the assigned structure. $^{13}$C-NMR (CDCl$_3$): δ 159.0 (C=O), 40.47 and 40.45 (C-1 and C-1'), 31.8 (C-6 and C-3'), 30.4 (C-2),30.1 (C-2'), 29.3 (C-4), 29.2 (C-5), 27.0 (C-3), 22.5 (C-7), 22.4 (C-4'), 13.9 (C-8 and C-5'); important infrared absorption bands (KBr disc) are present at 3334 (s, N—H), 1617 (vs, C=O), and 1579 (vs, amide II) cm$^{-1}$.

EXAMPLE 3
Synthesis of 1-Cyclohexyl-3-cyclooctylurea

Cyclooctylamine, 0.382 g (3.00 mmol), 0.40 mL (0.39 g, 3.1 mmol) of cyclohexylisocyanate in 20 mL of hexane, on standing for one day provides 0.664 g (88%) of 1-cyclohexyl-3-cyclooctylurea as white needles, mp 194.0–194.5° C. An infrared spectrum [3344 (s, NH), 3334 (s, NH), 1624 (vs, C=O), 1564 (vs. amide II) cm$^{-1}$] and mass spectrum [FAB-MS m/z calcd. for C$_{15}$H$_{28}$N$_2$O: 252, obsd: 253 (M+H$^+$)] confirms the identity of this material.

EXAMPLE 4
Cyclohexylcarbamothioic Acid 5-Cyclohexyl Ester

To a solution of 0.61 mL (0.58 g, 5.0 mmol) of cyclohexylthiol in 25 mL of hexane is slowly added a solution of 0.626 g (5.00 mmol) of cyclohexylisocyanate in 5 mL of hexane. Adding one drop of 1,8-diazabicyclo[5.4.0]undec-7-ene initiates the formation of a white crystalline product. After several days at ambient temperature, the mixture is cooled, the cyclohexylcarbamothioic acid S-cyclohexyl ester is collected, washed with ice-cold hexane and dried to provide a 1.15 g (4.76 mmol, 95%) of product melting at 117.0–118.0° C. A confirmatory $^{13}$C-NMR (CDCl$_3$) is observed for this material: 67 165.9 (C=O), 50.3 (C-1), 43.4 (C-1'), 33.8 (C-2', 6'), 33.1 (C-2, 6), 26.0 (C-3', 5') 25.5 (C-4$^1$), 25.4 (C-4), 24.7 (C-3, 5). Supportive infrared bands (KBr) are observed at 3343 (s, N—H), 1649 (vs, C=O), and 1206 (m, C—N) cm$^{-1}$.

EXAMPLE 5
Assay to Determine Inhibition of Soluble EH

Recombinant mouse sEH (MsEH) and human sEH (HsEH) were produced in a baculovirus expression system as previously reported. Grant et al., *J. Biol. Chem.*, 268, pp. 17628–17633 (1993); Beetham et al., *Arch. Biochem. Biophys.*, 305, pp. 197–201 (1993). The expressed proteins were purified from cell lysate by affinity chromatography. Wixtrom et al., *Anal. Biochem.*, 169, pp. 71–80 (1988). Protein concentration was quantified using the Pierce BCA assay using bovine serum albumin as the calibrating standard. The preparations were at least 97% pure as judged by SDS-PAGE and scanning densitometry. They contained no detectable esterase or glutathione transferase activity which can interfere with the assay. The assay was also evaluated with similar results in crude cell lysates or homogenate of tissues.

The $IC_{50}$s for each inhibitor were determined by the spectrophotometric assay of Dietze et al. (Dietze et al., "Spectrophotometric Substrates for Cytosolic Epoxide Hydrolase," *Anal. Biochem.*, 216, pp. 176–187, 1994) using cloned epoxide hydrolase genes expressed in the baculovirus system using racemic 4-nitrophenyl-trans-2,3-epoxy-3-phenylpropyl carbonate (NEP2C) as substrate. In a styrene 96-well microplate, 20 μl of enzyme preparation and 2 μl of the inhibitor solution in DMF ([I]final: 0.05 to 500 μM) were added to 180 μl of sodium phosphate (0.1 M, pH 7.4) containing 0.1 mg/ml of BSA. The mixture was incubated at 30° C. for 5 minutes. A substrate concentration of 40 μM was then obtained by adding 4 μl of a 2 mM solution. Activity was assessed by measuring the appearance of the 4-nitrophenolate at 405 nm at 30° C. for 1 minute (Spectramax 200; Molecular Device Inc., USA). Assays were performed in quadruplicate. By definition, the $IC_{50}$ is the concentration of inhibitor which reduces enzyme activity by 50%. $IC_{50}$s were determined by regression of at least five datum points with a minimum of two points in the linear region of the curve on either side of the $IC_{50}$. The curve was generated from at least four separate runs to obtain the standard deviation. In at least one run compounds of similar potency were included to insure rank order. A further rank order among very good compounds was determined with the $^3$H trans-stilbene oxide assay as described in Wixtrom and Hammock (below) or a related assay based on Borhan et al., "Improved Radiolabeled Substrates for Soluble Epoxide Hydrolase," *Anal. Biochem.*, 231, pp. 188–200, 1995. A similar partition assay based on $^3$H cis-stilbene oxide is described in Wixtrom and Hammock, "Membrane-Bound and Soluble-Fraction Epoxide Hydrolases: Methodological Aspects," *Biochemical Pharmacology and Toxicology*, Vol. 1, (Zakim and Vessey, eds.), John Wiley & Sons, Inc., New York, pp. 1–93, 1985.

EXAMPLE 6

Effect on Other Enzymes

Mammalian microsomal EH was assayed using $^3$H-cis-stilbene oxide, insect microsomal EH was assayed with 3H-juvenile hormone III, and $^3$H-trans-diphenyl-propene oxide, mammalian and plant cytosolic, and peroxisomal EHs were assayed using $^3$H-trans-diphenyl-propene oxide, P-450 was assayed using $^3$H-testosterone, carboxylic esterase assay used para-nitrophenylacetate, and gluthatione-S-transferase assay used chlorodinitrobenzene. Pepsin was assayed using hemoglobin as substrate.

It is to be understood that while the invention has been described above in conjunction with preferred specific embodiments, the description and examples are intended to illustrate and not limit the scope of the invention, which is defined by the scope of the appended claims.

What is claimed is:

1. A method of treating an epoxide hydrolase, useful to purify, isolate, or inhibit the epoxide hydrolase, comprising: providing a compound having the structure

FORMULA 1 wherein X and Y is each independently nitrogen, oxygen, or sulfur, and X can further be carbon, at least one of $R_1$–$R_4$ is hydrogen, $R_2$ is hydrogen when X is nitrogen but is not present when X is sulfur or oxygen, $R_4$ is hydrogen when Y is nitrogen but is not present when Y is sulfur or oxygen, $R_1$ and $R_3$ is each independently H, $C_{1-20}$ substituted or unsubstituted alkyl, cycloalkyl, aryl, acyl, or heterocyclic, the compound provided being in free form or being derivatized so as to be immobilized to a water insoluble support; and, contacting the free form or immobilized compound with an epoxide hydrolase under conditions in which the epoxide hydrolase is enzymatically active, the contacting effective to form a complex between the compound and the epoxide hydrolase, wherein the activity of the epoxide hydrolase so complexed is modified with respect to enzymatically active, uncomplexed epoxide hydrolase.

2. The method as in claim 1 wherein the providing step includes converting a precursor form of the compound before forming the complex.

3. The method as in claim 2 wherein the precursor form of the compound is a carbodiimine or thiourea.

4. The method as in claim 1 where the compound is capable of establishing anionic bond with a carboxylic acid residue of a protein, to stabilize one or more hydrogen bonds or to have a group able to establish a hydrogen bond with a tyrosine residue over the catalytic site.

5. The method as in claim 1 wherein the modified activity of the epoxide hydrolase when in the complex is epoxide hydrolase inhibition.

6. The method as in claim 1 wherein the epoxide hydrolase of the complex is selectively formed with a soluble epoxide hydrolase.

7. The method as in claim 1 wherein the treating is useful for purification or isolation of a microsomal epoxide hydrolase, and the compound is derivatized so as to be immobilized to a water insoluble support.

8. The method as in claim 7 wherein the compound is immobilized through derivatization at one of $R_1$ or $R_3$.

9. The method as in claim 7 wherein the contacting includes eluting an aqueous solution through the water insoluble support.

10. The method as in claim 1 wherein the treating is useful for inhibiting a mammalian soluble or microsomal epoxide hydrolase.

11. The method as in claim 10 wherein the compound has an $IC_{50}$ of less than about 500 μM.

12. The method as in claim 10 wherein the treating is therapeutically effective to treat an inflammation.

13. The method as in claim 12 wherein the inflammation treated is adult respiratory distress syndrome.

14. The method as in claim 10 wherein the treating is in conjunction with a cancer therapy.

15. The method as in claim 10 wherein an effective therapeutic amount of the compound provided is a total daily dose from about 0.001 μM/kg to about 100 mg/kg body weight of the mammal.

16. The method as in claim 10 wherein the compound reduces the conversion of lipid epoxides to the corresponding diols.

17. The method as in claim 1 wherein the treating is useful for inhibiting a plant epoxide hydrolase.

18. The method as in claim 17 wherein the compound is provided in combination with a plant growth regulator or an herbicide.

19. The method as in claim 1 wherein the treating is useful for inhibition of an insect epoxide hydrolase or a fungal epoxide hydrolase.

20. The method as in claim 19 wherein the compound is provided in combination with an insect growth regulator or an insecticide.

21. The method as in claim 1 wherein the treating is useful to reduce mycotoxic production by fungi.

22. The method as in claim 21 wherein the compound is provided in combination with a fungicide.

23. A purification method for an epoxide hydrolase, comprising:

immobilizing a compound having the structure wherein Z is oxygen or sulfur, W is carbon or sulfur, X and Y is each independently nitrogen, oxygen, or sulfur, and X can further be carbon, at least one of $R_1$–$R_4$ is hydrogen, $R_2$ is hydrogen when X is nitrogen but is not present when X is sulfur or oxygen, $R_4$ is hydrogen when Y is nitrogen but is not present when Y is sulfur or oxygen, $R_1$ and $R_3$ is each independently $C_{1-20}$ substituted or unsubstituted alkyl, cycloalkyl, aryl, acyl, or heterocyclic, to a water-insoluble support; and eluting an aqueous solution having an epoxide hydrolase therein through the support.

24. The method as in claim 23 wherein the eluting causes a selective separation of soluble epoxide hydrolase.

25. An affinity separations article, comprising:

a water insoluble support defining an exposed surface and having an immobilized compound thereon, the immobilized compound being derived from a compound having the structure

FORMULA 1 wherein X and Y is each independently nitrogen, oxygen, or sulfur, and X can further be carbon, at least one of $R_1$–$R_4$ is hydrogen, $R_2$ is hydrogen when X is nitrogen but is not present when X is sulfur or oxygen, $R_4$ is hydrogen when Y is nitrogen but is not present when Y is sulfur or oxygen, $R_1$ and $R_3$ is each independently $C_{1-20}$ substituted or unsubstituted alkyl, cycloalkyl, aryl, acyl, or heterocyclic, the compound being derivatized for immobilization through one of $R_1$ or $R_3$, the immobilized compound capable of forming a complex with an epoxide hydrolase.

26. The article as in claim 25 wherein the immobilized compound is derivatized through $R_3$ and wherein $R_1$ is cyclohexyl.

* * * * *